United States Patent
Pedrani

(10) Patent No.: US 10,328,035 B2
(45) Date of Patent: Jun. 25, 2019

(54) MODIFIED-RELEASE THERAPEUTIC SYSTEMS FOR ORAL ADMINISTRATION OF MENTHOL IN THE TREATMENT OF INTESTINAL DISORDERS

(71) Applicant: MOGON PHARMACEUTICALS SAGL, Melide (CH)

(72) Inventor: Massimo Pedrani, Melide (CH)

(73) Assignee: MOGON PHARMACEUTICALS SAGL, Melide (CH)

( * ) Notice: Subject to any disclaimer, the term of this patent is extended or adjusted under 35 U.S.C. 154(b) by 219 days.

(21) Appl. No.: 15/103,192

(22) PCT Filed: Dec. 10, 2014

(86) PCT No.: PCT/IB2014/066763
§ 371 (c)(1),
(2) Date: Jun. 9, 2016

(87) PCT Pub. No.: WO2015/087258
PCT Pub. Date: Jun. 18, 2015

(65) Prior Publication Data
US 2018/0133166 A1    May 17, 2018

(30) Foreign Application Priority Data
Dec. 11, 2013 (IT) .............................. MI2013A2066

(51) Int. Cl.
| | | |
|---|---|---|
| A61K 9/20 | (2006.01) | |
| A61K 31/045 | (2006.01) | |
| A61K 9/28 | (2006.01) | |
| A61K 45/06 | (2006.01) | |
| A61P 1/00 | (2006.01) | |

(52) U.S. Cl.
CPC ............ *A61K 31/045* (2013.01); *A61K 9/205* (2013.01); *A61K 9/2031* (2013.01); *A61K 9/2054* (2013.01); *A61K 9/2059* (2013.01); *A61K 9/2077* (2013.01); *A61K 9/282* (2013.01); *A61K 9/286* (2013.01); *A61K 9/288* (2013.01); *A61K 9/2846* (2013.01); *A61K 9/2866* (2013.01); *A61K 45/06* (2013.01); *A61P 1/00* (2018.01)

(58) Field of Classification Search
None
See application file for complete search history.

(56) References Cited

U.S. PATENT DOCUMENTS

2004/0126358 A1 * 7/2004 Warne .................. A61K 9/2886
424/85.2
2012/0207842 A1 8/2012 Shah et al.

FOREIGN PATENT DOCUMENTS

WO    2011002972 A2    1/2011

OTHER PUBLICATIONS

Gazzaniga A., et al., "Time-controlled oral delivery systems for colon targeting", Expert Opinion on Drug Delivery, Informa Healthcare, GB, vol. 3, No. 5, Jan. 1, 2006, pp. 583-597.
Grigoleit G., et al., "Gastrointestinal clinical pharmacology of peppermint oil", Phytomedicine, Gustav Fischer Verlag, Stuttgart, DE, vol. 12, No. 8, Aug. 2, 2005, pp. 607-611.
Mirela Nadler Milabuer, et al., "Orally administered drug delivery systems to the colon", Oral controlled release formulation design and drug delivery: theory to practice, Jan. 1, 2010, pp. 225-243.
Search Report and Written Opinion of PCT/IB2014/066763 dated Mar. 23, 2015.

* cited by examiner

*Primary Examiner* — Nannette Holloman
(74) *Attorney, Agent, or Firm* — Silvia Salvadori, P.C.; Silvia Salvadori

(57) ABSTRACT

Disclosed are colon-specific delayed-release pharmaceutical compositions comprising: a) a matrix wherein micronized menthol with a particle-size distribution ranging between 100 nm and 1200 μm is dispersed b) a gastro-resistant or acid-resistant pH-independent coating with a lag time of matrix a).

11 Claims, No Drawings

MODIFIED-RELEASE THERAPEUTIC SYSTEMS FOR ORAL ADMINISTRATION OF MENTHOL IN THE TREATMENT OF INTESTINAL DISORDERS

This application is a U.S. national stage of PCT/IB2014/066763 filed on 10 Dec. 2014, which claims priority to and the benefit of Italian Application No. MI2013A002066 filed on 11 Dec. 2013, the contents of which are incorporated herein by reference in their entireties.

The present invention relates to modified-release compositions containing menthol incorporated in hydrophilic matrices of hydroxypropylmethylcellulose loaded into a monolithic system with gastro-resistant coating.

The compositions according to the invention modulate the activity of menthol, reducing its administration frequency and modulating its release in particular sites of the gastrointestinal tract.

The compositions according to the invention are useful in the treatment of intestinal disorders of inflammatory, immunological and/or systemic origin, in particular in the treatment of irritable bowel syndrome.

PRIOR ART

The use of peppermint in the treatment of symptoms of irritable bowel syndrome (IBS), in particular cramps of the gastrointestinal tract, flatulence and abdominal pains, has been confirmed and consolidated by numerous studies in recent years. The spasmolytic effect of peppermint oil on the smooth muscles of the digestive tract is well known. Said effect has been variously demonstrated in vitro and in vivo, especially on the smooth muscle fibres of the colon. The ingredient primarily responsible for the effects of peppermint oil is menthol, which presents a marked spasmolytic effect attributable to the following action mechanisms:

- inhibition of the $Ca^{2+}$ channels present on the smooth muscle cells, which are involved in the contraction mechanism;
- colonic activation of the TRPM8 (Transient Receptor Potential Channel) receptors which induce a lasting relaxation effect on the colon muscles (known as cold receptors);
- inhibition of the TRPA1 receptors, which induce proximal and distal contraction of the colon.

In view of these properties, a particularly desirable objective is colon-specific release of menthol starting from the distal ileum with a suitable lag time until the distal part of the small intestine is reached, thus ensuring slow, gradual, constant release of the product throughout the colonic tract.

Essential oil of mint formulations characterised by a gastro-resistant coating are known and already available on the market. However, the release profile of the known formulations is unsatisfactory, because it does not guarantee homogenous release throughout the colonic tract.

US 2012/207842 discloses a multi-particulate delayed-release system with a gastro-resistant coating (2 hours at pH 1.2), with rapid release at a neutral pH (over 80% of the menthol within 2 hours at most). The core does not present a modified-release system, but immediate release or modest release control (45 minutes to 2 hours). Said document requires the use of hydroxypropylmethylcellulose in the core and the subcoating, not for the purpose of release control but as binder to obtain the granules and as coating agent in the final film-coating.

WO 01/76392 discloses a composition containing garlic as active ingredient with an enteric coating. The active ingredient is released rapidly in the small intestine. The composition can contain peppermint extract (not pure menthol) as deodoriser. Mint oil is present in the outer enteric film-coating, and is therefore not subject to any release control in the enteric environment, into which the extract is thus released immediately. Said document therefore does not disclose a colon-specific delayed-release formulation of menthol, still less a formulation wherein menthol is dispersed in a hydrophilic matrix.

CN 102008547 discloses capsules containing *Mentha rotundifoliae* oil (which has an insignificant menthol content) coated with acrylic resins. Thus not only does it not refer to crystalline menthol, but the formulations described in said document do not have any effect of delaying the release of the active ingredient in the colon, only gastro-resistance.

DESCRIPTION OF THE INVENTION

It has now been found that an optimum colon-specific slow release of menthol can be obtained with monolithic pharmaceutical compositions comprising:

a) a core containing hydroxypropylmethylcellulose wherein the menthol is dispersed in ground, co-ground or micronised form with a particle size ranging between 100 nm and 1200 μm;

b) a gastro-resistant coating of core a).

The formulations according to the invention, characterised by a core with a monolithic matrix, are able to modulate, control and slow the release of the active ingredient within 8-24 hours. The gastro-resistant coating of the core prevents release in vitro for at least 2 hours under conditions of pH <1.2-5.5.

The gastro-resistant coating typically consists of cellulose derivatives, cellulose phthalates, succinates, methacrylic or polymethacrylic acid polymers, shellac or alginates, preferably of shellac and hydroxypropylmethylcellulose, or ethylcellulose with alginic acid, or polymethacrylates (pH-dependent), or simple ethylcellulose and/or hydroxypropylmethylcellulose (pH-independent/lag time). A mixture of shellac and hydroxypropylmethylcellulose is particularly preferred.

The matrix core is coated with a quantity of polymer/resin sufficient to guarantee that it remains intact in gastric and enteric juice for at least 2-4 hours before the release of the active ingredient from the core (lag time). To reduce the impact of the variability of gastric voiding times, the formulations can include a further gastro-resistant coating (pH-dependent) external to the matrix core (pH-independent) and to the cellulose film-coating (pH-independent), to further delay contact between the biological fluids and the modified-release core (extended release).

In this way the system prevents early release during the stomach-jejunum transit time, and slow release up to 24 hours is obtained to ensure homogenous distribution of the medicament in the ascending, transverse and descending tracts of the large intestine.

The compositions according to the invention therefore differ from the usual delayed-release forms (gastro-resistant and/or with lag time), which can reach the distal part of the ileum and/or the initial part of the colon, but then rapidly release the active constituent without being distributed evenly in the colonic tract.

The use of hydroxypropylmethylcellulose with different rheological characteristics (viscosity/swelling properties) of the matrix core allows the release to be modulated in a gradual, programmed way for between 8 and 24 hours. The hydroxypropylmethylcellulose usable according to the invention has an apparent viscosity measured at 20° C. in 2% aqueous solution ranging between 3 and 200,000 mPs, preferably between 30 and 150,000, and more preferably between 50 and 100,000. A single type of hydroxypropylmethylcellulose, or a mixture of at least two types of hydroxypropylmethylcellulose with different viscosities, can be used. Hydroxypropylmethylcellulose is available on the market from Dow Chemical under the Methocel brands, or from Ashland under the Benecel brands. Preferred examples of hydroxypropylmethylcellulose are those having the same characteristics as the commercial products Methocel K100lv, K15M, K4M and K100M. The use of a hydroxypropylmethylcellulose having a viscosity similar to that of Methocel K100 lv, ranging between 78 and 117 mPas (again at 20° C. in 2% aqueous solution) is particularly preferred.

The compositions according to the invention will generally contain a unit dose ranging between 10 and 1200 mg of menthol, preferably 50-200 mg of menthol.

The weight ratio between menthol and hydrophilic matrix ranges between 1:5 and 4:1 (preferably 1:3).

The compositions according to the invention can also contain other excipients, such as wetting agents, ionic or non-ionic surfactants, disintegrating agents, super-disintegrating agents, crosslinked polymers, complexing agents and lubricants.

Examples of said excipients include phosphatides, lecithins, sodium lauryl sulphate, sorbitan esters, sucrose palmitate, sodium lauryl sarcosinate, cholic acids, poloxamer, cyclodextrins, starches, sodium starch glycolate, croscarmellose and crosslinked polyvinylpyrrolidones.

The hydrophilic matrix of hydroxypropylmethylcellulose can optionally be modified by adding lipophilic ingredients (fatty acids, fatty alcohols, triglycerides), water-soluble ingredients (polyols, mannitol, lactose, trehalose), water-dispersible ingredients (microcrystalline cellulose) or water-insoluble ingredients (dibasic calcium phosphate, calcium and magnesium salts) to modulate the release kinetics.

The compositions according to the invention maximise the pharmacological effect of menthol in the treatment of irritable bowel syndrome, due to their ability to carry the active ingredient and specifically release it in the colon. The gastro-resistant coating must ensure the maintenance of the structure for about 1-2 hours at pH 1.2, with a controlled-release profile in the next 8-24 hours at pH 7.2, thus ensuring pharmacological coverage from the ascending tract to the transverse and descending tract of the colon.

For the intended use, it is important to guarantee controlled release starting from the terminal tract of the ileum and continuing through the entire colonic tract. It is also necessary to guarantee a certain homogeneity of the quantity released over time and simultaneously allow its activity at both topical and systemic level when a proportion of the active ingredient has been released. The compositions according to the invention are therefore particularly useful for the treatment of acute and chronic gastrointestinal disorders such as irritable bowel syndrome (IBS), diarrhoea, constipation, Crohn's disease, ulcerating colitis, and bowel disease (IBD) in general.

Conventional techniques such as direct compression, wet granulation, dry compacting/granulation and melt granulation can be used to prepare the compositions according to the invention.

As menthol presents as a large crystal, it cannot be handled as such for the preparation and production of the different pharmaceutical forms, and must therefore be subjected to an activation process by grinding and/or micronisation and/or co-grinding of the product, either alone or loaded with some inert diluent excipients.

The product, which originally presents in the form of translucent crystals with dimensions of a few centimeters, is suitably ground, micronised and/or co-ground with other functional excipients such as celluloses, starches, dextrins, calcium phosphate, polyols, colloidal silicon dioxides and other diluents, to obtain a product with dimensions ranging between 100 nm and 1200 µm; preferably between 50 and 700 µm.

The product thus treated, optionally with the addition of excipients such as wetting agents, surfactants, disintegrating agents, super-disintegrating agents, glidants, non-stick agents or lubricants, is then incorporated in the hydrophilic matrix using a suitable wet or dry granulation technique, direct partitioning, direct compression, co-grinding, melt granulation or extrusion granulation.

The outer coating, consisting of materials possessing gastroresistance and/or release properties in different intestinal pHs (pH-dependent) and/or pH-independent lag time properties (delayed-release), is then applied to the core thus obtained. According to a general embodiment of the invention, a hydrophilic matrix is first prepared, comprising one or more types of hydroxypropylmethylcellulose wherein micronised, ground or co-ground menthol is dispersed. Any functional excipients required to dilute the product and make it workable are then added by different pharmaceutical processes. The ratio of active ingredient to matrix can range between 1:1 and 1:9, and the ratio of active ingredient to excipient should not normally exceed 1:4; the optimum quantity is between 0.1% and 50%.

A variable quantity of diluents up to 50%, lubricants (0.5-3%), glidants (0.5-3%), disintegrating and super-disintegrating agents (0.1-40%) and complexing agents (0.1-40%) may be added to this mixture.

The compositions according to the invention may also contain other active ingredients with synergic, complementary or otherwise useful activities. Examples of said active ingredients include probiotics (lactobacilli, bifidobacteria), digestive enzymes (enteric juices), prebiotics (butyrates, propionates, medium-long chain fatty acids, omega-3 fatty acids or esters), fibres (psyllium, guar gum, acacia fibres, calcium polycarbophil), antispastics (trimebutine and the salts thereof, otilonium bromide and other salts, dicyclomine and the salts thereof, tiropramide, propantheline and the salts thereof, biperiden and the salts thereof, octatropine and the salts thereof, memantine and ditropan), medicaments active in IBS and IBD such as anti-inflammatories (mesalazine, corticosteroids, azathioprine, mercaptopurine, alpha-lipoic acid), drugs active in IBS (lubiprostone, linaclotide), extracts or active constituents of plant origin (artichoke, astaxanthin, camomile, curcumin, boswellia, green tea, echinacea), lactoferrin, and antibiotics with a local topical action such as rifaximin and rifamycin.

In terms of dissolution characteristics, contact between the compositions described above and water or enteric biological fluids generates delayed, site-specific release of the active ingredient. The excipients and polymers present in the structure regulate the wettability of the system and the homogenous dissolution of menthol within limited release ranges, thus promoting its localised activity and continuous, gradual absorption in the gastrointestinal tract.

The following examples illustrate the invention in greater detail.

Example 1

50 g of activated menthol is loaded into a mixer/granulator with 200 g of dibasic calcium phosphate, 200 g of microcrystalline cellulose and 150 g of mannitol.

2 g of crospovidone, 8 g of lecithin and 150 g of hydroxypropylmethylcellulose (HPMC K100 lv) are added in sequence to the same system.

The ingredients are mixed until a homogenous dispersion of the matrices is obtained, and 5 g of magnesium stearate and 5 g of colloidal silicon dioxide are then added in sequence.

The final mixture is compressed to a unit weight of 770 mg/tablet in order to administer 50 mg of active ingredient per tablet.

The resulting tablets are then film-coated with a gastro-resistant solution/suspension based on 30 g of shellac (25%), 12 g of hydroxypropylmethylcellulose and 6 g of glycerin, so that a tablet with a mean weight of 818 mg is obtained.

The tablets remain intact for at least 2 hours when subjected to a disintegration test at pH 1.2. When subjected to a dissolution test at pH 7.2 they exhibit the following release profile: not more than 20% after 60 minutes, not more than 60% after 240 minutes, and not more than 80% after 480 minutes; in any event, the value must be >70% after 24 hours.

Example 2

50 g of activated menthol is loaded into a granulator/homogeniser, and 55 g of mannitol is added.

100 g of hydroxypropylmethylcellulose (HPMC K 100 lv), 55 g of hydroxypropylmethylcellulose (K4M) and 50 mg of microcrystalline cellulose are added to the same granulator.

The ingredients are mixed until a homogenous dispersion of the matrices is obtained, and 210 g of calcium phosphate, 3 g of magnesium stearate and 5 g of colloidal silicon dioxide are then added in sequence.

The final mixture is compressed to a unit weight of 530 mg/tablet in order to administer 50 mg of active ingredient per tablet.

The resulting tablets are then film-coated with a gastro-resistant solution/suspension based on 20 g of shellac (25%) 20, 8 g of hydroxypropylmethylcellulose and 2 g of glycerin, so that a tablet with a mean weight of 560 mg is obtained.

The tablets remain intact for at least 2 hours when subjected to a disintegration test at pH 1.2. When subjected to a dissolution test at pH 7.2 they exhibit the following release profile: not more than 10% after 60 minutes, not more than 40% after 240 minutes, and not more than 70% after 480 minutes; in any event, the value must be >70% after 24 hours.

Example 3

800 g of menthol is loaded into a granulator/homogeniser, and 200 g of hydroxypropylmethylcellulose (K100 lv), 200 g of hydroxypropylmethylcellulose (K15M), 480 g of mannitol and 252 g of microcrystalline cellulose are added.

The ingredients are mixed for at least 15 minutes to obtain a homogenous mixture.

8 g of croscarmellose, 40 g of lecithin, 40 g of colloidal silicon dioxide and 20 g of magnesium stearate are then added in sequence.

The final mixture is compressed to a unit weight of 510 mg/tablet in order to administer 200 mg of active ingredient per tablet.

The cores obtained are coated with 500 g of shellac (aquagold 25%), 50 g of hydroxypropylmethylcellulose and 25 g of glycerin. A gastro-resistant film-coating with about 50 mg of coating per tablet is obtained.

When subjected to a dissolution test at pH 1.2 and then at pH 7.2, the tablets exhibit the following release profile: at pH 1.2: 0% after 120 minutes; at pH 7.2: not more than 25% after 60 minutes, not more than 50% after 180 minutes, and not more than 80% after 8 hours; >80% after 12 hours.

Example 4

800 g of menthol is loaded into a granulator/homogeniser, and 200 g of hydroxypropylmethylcellulose, 200 g of polyoxyethylene oxide (PEO-20NF), 480 g of mannitol and 252 g of microcrystalline cellulose are added.

The ingredients are mixed for at least 15 minutes to obtain a homogenous mixture.

8 g of croscarmellose, 40 g of lecithin, 40 g of colloidal silicon dioxide and 20 g of magnesium stearate are then added in sequence.

The final mixture is compressed to a unit weight of 510 mg/tablet in order to administer 200 mg of active ingredient per tablet.

The cores obtained are coated with an aqueous dispersion containing 80 g of ethylcellulose, 16 g of sodium alginate, 2 g of titanium dioxide and 2 g of stearic acid. A film-coating with about 25 mg of coating per tablet is obtained.

When subjected to a dissolution test, the tablets exhibit the following release profile: at pH 1.2: <10% after 120 minutes; at pH 7.2: not more than 25% after 60 minutes, not more than 60% after 180 minutes, and not more than 80% after 8 hours; >80% after 24 hours.

Example 5

500 g of activated menthol is loaded into a mixer/granulator with 350 g of dibasic calcium phosphate.

2 g of crospovidone and 150 g of hydrophilic matrix hydroxypropylmethylcellulose (HPMC 15M) are added in sequence to the same system.

The ingredients are mixed until a homogenous dispersion of the matrices is obtained; 5 g of magnesium stearate, 5 g of colloidal silicon dioxide and 8 g of glyceryl behenate are then added in sequence.

The final mixture is compressed to a unit weight of 1020 mg/tablet in order to administer 500 mg of active ingredient per tablet.

The resulting tablets are then film-coated with a gastro-resistant solution/suspension based on 160 g of shellac (25%), 20 g of hydroxypropylmethylcellulose and 8 g of glycerin.

The tablets remain intact for at least 2 hours when subjected to a disintegration test at pH 1.2. When subjected to a dissolution test at pH 7.2 they exhibit the following release profile: not more than 35% after 60 minutes, not more than 65% after 240 minutes, and not more than 80% after 480 minutes; in any event, the value must be >80% after 24 hours.

The invention claimed is:

1. Monolithic colon-specific delayed release pharmaceutical compositions comprising:
    a) a core with a monolithic matrix comprising hydroxypropylmethylcellulose wherein menthol is dispersed in ground, co-ground, micronized form with a particle size ranging from 100 nm to 1200 μm,
    b) a gastro-resistant coating of the core a),
    wherein the menthol to hydroxypropylmethylcellulose weight ratio ranges from 1:5-4:1.

2. Compositions according to claim 1 wherein the hydroxypropylmethylcellulose in the core has apparent viscosity at 20° C. in 2% water solution ranging from 3 to 200.000 mPas.

3. Compositions according to claim 1 wherein the core comprises a mixture of at least two hydroxypropylmethylcelluloses having different apparent viscosity values.

4. Compositions according to claim 1 comprising only one hydroxypropylmethylcellulose having apparent viscosity at 20° C. in 2% water solution ranging from 80 to 120 mPas.

5. Compositions according to claim 1 wherein the gastro-resistant coating comprises cellulose derivatives, methacrylic acid polymers, shellac, alginates or mixtures thereof.

6. Compositions according to claim 4 wherein the gastro-resistant coating consists of shellac and hydroxypropylmethylcellulose, or ethylcellulose and alginic acid, or polymethacrylates or cellulose acetophthalate.

7. Compositions according to claim 1 comprising 50 to 1200 mg of menthol.

8. Compositions according to claim 1 further comprising excipients selected from wetting agents, ionic or non-ionic surfactants, water soluble diluents, water dispersible diluents, water insoluble diluents, disintegrants, lubricants, glidants, coloring agents.

9. Compositions according to claim 8 wherein said excipients are selected from phosphatides, lecithins, sodium lauryl sulfate, sorbitan esters, sucrose palmitate, sodium laurylsarcosinate, cholic acids, poloxamer, cyclodextrins, starches, sodium starch glycolate, croscarmellose, cross-linked polyvinylpyrrolidone, polyols, microcrystalline celluloses, dibasic calcium phosphate, calcium and magnesium salts.

10. Compositions according to claim 1 further comprising one or more ingredients selected from probiotics, digestive enzymes, prebiotics, fibres, antispastics, antiinflammatories, IBS and IBD-active medicaments, extracts or active principles of vegetable origin, local antibiotics.

11. Method of treating Intestinal Bowel Syndrome (IBS) and intestinal bowel diseases in subjects in need thereof, said method comprising
   administering to said subjects an effective amount of the compositions according to claim 1; and
   treating said subjects of said IBS and of said intestinal bowel diseases.

* * * * *